United States Patent [19]
Weissman

[11] Patent Number: 6,051,733
[45] Date of Patent: Apr. 18, 2000

[54] SULFUR-CONTAINING COMPOUNDS FOR OPTICAL GRADE POLYMERIC CASTING COMPOSITIONS

[75] Inventor: Peter Weissman, Marietta, Ga.

[73] Assignee: UCB, S.A., Brussels, Belgium

[21] Appl. No.: 08/860,594

[22] PCT Filed: Feb. 22, 1996

[86] PCT No.: PCT/BE96/00017

§ 371 Date: Jul. 25, 1997

§ 102(e) Date: Jul. 25, 1997

[87] PCT Pub. No.: WO96/26184

PCT Pub. Date: Aug. 29, 1996

[51] Int. Cl.$^7$ ................................................. C07C 321/00
[52] U.S. Cl. ............................................ 560/152; 560/153
[58] Field of Search ........................................ 560/152, 153

[56] References Cited

U.S. PATENT DOCUMENTS

| 3,181,971 | 5/1965 | Raynor | 117/232 |
|---|---|---|---|
| 3,494,947 | 2/1970 | Schutze et al. | 260/481 |
| 3,629,194 | 12/1971 | Onishi et al. | 260/45.85 |
| 3,758,549 | 9/1973 | Dexter et al. | 260/491 R |
| 4,226,991 | 10/1980 | Nakahara et al. | 544/221 |
| 4,349,468 | 9/1982 | Nakahara et al. | 524/302 |

FOREIGN PATENT DOCUMENTS 1270114  4/1972  United Kingdom.

*Primary Examiner*—Bernard Lipman
*Attorney, Agent, or Firm*—Wenderoth, Lind & Ponack, L.L.P.

[57] ABSTRACT

Polymeric compositions for the preparation of optical grade materials, and the optical materials prepared thereby, are provided. The compositions include a class of reactive and non-reactive additives, referred to as additive, in combination with a polymer and optionally a diluent. The additives are preferably the reaction product of a thiol containing compound and an unsaturated compound. The additives optimally have a refractive index between about 1.40 and 1.70, and preferably between 1.50 and 1.70; a relatively high Abbe number (between 25 and 60) and minimal color.

9 Claims, No Drawings

SULFUR-CONTAINING COMPOUNDS FOR OPTICAL GRADE POLYMERIC CASTING COMPOSITIONS

This invention is in the area of polymeric compositions for the preparation of optical grade materials, and the optical materials, such as lenses, prepared thereby. The compositions include reactive or nonreactive additives in combination with polymeric materials and optional diluents. The reactive additives can be incorporated into polymer chains during polymerization to modify the properties of the polymer.

Polymers are often used in demanding applications such as matrix materials for advanced composites and as optical components, such as lenses. These materials require high strength and acceptable levels of flexibility and toughness. Three important properties of optical grade polymeric materials include the refractive index, the relative dispersion and color.

The refractive index of a material is the ratio of the velocity of light through a vacuum to the velocity of light through the material. The refractive index is not a constant over the spectrum of light, but changes as a function of wavelength. This change in the refractive index is called dispersion. The refractive index of optical grade polymeric materials is generally tailored to meet very specific requirements. For example, when a polymer is mated with another material, such as during windshield repair or in the preparation of polymer/polymer or polymer glass composites, the refractive indices of the two materials must match almost exactly if the border between the two materials is to remain essentially invisible. High refractive index materials are useful in the production of thin high powered lenses.

Relative dispersion (or its reciprocal that is typically known as the Abbe number) is a measure of the refractive index's dependence on the wavelength of light. Optical grade polymeric materials should exhibit a minimal dependence of refractive index on wavelength (i.e. high Abbe number), and thus, have a low relative dispersion.

Optical grade polymeric materials should also exhibit minimal color.

Some sulfur containing materials reported to act as stabilizers in polymer systems include those disclosed in the following patent documents.

British Patent No. 1 270 114 discloses plasticized thermoplastic polymer compositions that contain a thermoplastic polymer, a polymerizable plasticizer, and a polythiol. The patent states that the mechanism by which the compositions are cured is not certain, but may involve the reaction of the polythiol with the polymerizable plasticizer to produce thioether links. The plasticizer is defined as a compound capable of free-radical initiated homopolymerization, which has two to five units of unconjugated unsaturation. The polythiol has two or more reactive —SH groups, and is preferably an ester of thioglycolic acid, α-mercaptopropionic acid, or β-mercaptopropionic acid with a polyhydroxy compound having two to six hydroxyl groups.

U.S. Pat. No. 4,226,991 discloses antioxidant stabilizers for polyolefin resins, produced by reacting an olefin of formula $R'RC=CH_2$, where R is alkyl and R' is H or alkyl (and wherein the sum of the number of carbon atoms in R and R' is from 4 to 38), with a mercaptopropionic acid and a polyol.

U.S. Pat. No. 4,349,468 discloses stabilizers for polyolefin resins, which are the reaction products of an alkylthiopropionic acid with a polyol. The alkylthiopropionic acid is the reaction product of an olefin of formula $R'RC=CH_2$, where R is alkyl and R' is an alkyl group (and wherein the sum of the number of carbon atoms in R and R' is from 4 to 26) or hydrogen, with a betamercaptopropionic acid compound of formula $HSCH_2CH_2COR''$, where R" is hydrogen or a lower alkyl group.

U.S. Pat. No. 3,181,971 discloses stabilizers for polypropylene which can prevent copper catalyzed degradation of the polypropylene. The stabilizer composition is a mixture of a phenolic antioxidant, a non-volatile primary or secondary amino compound, and an organic divalent sulfur compound. The exemplified sulfur containing compounds are alkyl esters of dithio propionates and dithio butyrates.

U.S. Pat. No. 3,629,194 discloses mercaptoester antioxidant stabilizers for polyolefins.

U.S. Pat. No. 3,758,549 discloses alkyl esters of alkylthioalkanoic acids used as antioxidants for a variety of materials, including organic polymeric substances.

European Application 0 453 149 A2 discloses a crosslinkable polymeric casting composition that includes a) a polyoxy alkylene glycol diacrylate or dimethacrylate; b) a monomer having a recurring unit derived from at least one radical-polymerizable bisphenol monomer capable of forming a homopolymer having a refractive index of more than 1.55; and c) a urethane monomer having 2 to 6 terminal groups selected from the group comprising acrylic and methacrylic groups.

EPA 0 598 551 A2 discloses a crosslinkable polymeric casting composition for optical lenses comprising 35 to 85% by weight, of an aromatic olefin monomer, 15 to 60% by weight of a polythio compound such as a polyol polyalkylthioester and optionally from 1 to 40% by weight of a polymerizable comonomer such as styrene or a polyoxyalkylene glycol poly(meth)acrylate. This composition however does not meet the required combination of high refractive index, low refractive dispersion and minimal color, presumably because it results from non-reactive mixing of the ingredients at room temperature.

Thus the technical problem to be solved by the present invention is to provide a composition suitable for lenses, possessing a combination of high refractive index, low refractive dispersion and minimal color, and at the same time which is able to be manufactured at an accelerated speed versus prior art compositions, thereby improving the productivity of making lenses and hence improving their manufacturing cost and their time of delivery to customers.

It is therefore an object of the invention to provide an additive for use in polymeric compositions with acceptable optical properties, in particular which enhance the refractive index of the material without adversely affecting its color and refractive dispersion.

It is another object of the invention to provide a polymeric material with excellent optical properties and acceptable flexibility and toughness.

It is still another object of the invention to provide an additive that has a high refractive index, an Abbe number between 25 and 60 and minimal color.

It is yet another object of the present invention to provide a highly reactive polymeric composition which allows the manufacture of optical materials within a reduced period of time while maintaining the overall level of performance of the materials.

Polymeric compositions for the preparation of optical grade materials, and the optical materials prepared thereby, are provided. The compositions contain a class of reactive and non-reactive additives, in combination with a polymer and optionally a diluent. The additives are preferably the reaction product of a thiol containing compound and an unsaturated compound.

The additives optimally have a refractive index between about 1.40 and 1.70, and preferably between 1.50 and 1.70; a relatively high Abbe number (between about 25 and 60) and minimal color. Preferably, the additives have an Abbe number in the range from about 34 to 48. For some applications, additives exhibiting an Abbe number of between 34 and 40 are sufficient. By appropriate selection of the polythiol and unsaturated compound, additives can be prepared that have a refractive index that is higher than the reactants used to prepare it. The additive should also exhibit minimal color (i.e., a color in the CIE system wherein a is greater than −0.5 and b is less than +2.0, and preferably, less than +1.5). Further, the additives are noncrosslinked and are liquids at at least 60° C., and preferably at least 40° C.

These adddditives can be incorporated into polymeric material without adversely affecting the optical properties of the polymer. By appropriate selection of the polymer and the additive, the polymeric composition itself can also exhibit a refractive index of 1.50 and 1.70, an Abbe number in the range of 25 and 60, and more typically, between 30 to 52, and minimal color.

The additives can be reactive or non-reactive. Non-reactive additives are those in which all of the —SH groups have been reacted with an unsaturated compound (or otherwise protected), and the resulting compound contains no additional reactive groups. These compounds do not react with the monomers or oligomers during the polymerization reaction, but instead impart desired characteristics to the optical polymeric composition or optical grade product.

The reactive additives of the present inventions are additives in which either not all of the —SH groups have been reacted with the unsaturated compound (or otherwise protected) or the —SH groups have been reacted with an unsaturated compound which contains an additional functional group which is capable of reacting with monomers, polymers or oligomers, for example, an unsaturated monomer which also contains an —OH group. The free —SH group will react with, for example, unsaturated monomers, oligomers or polymers under appropriate conditions, for example, free radical or nucleophilic polymerization. If the reactive additive has one free —SH group, it will act as a chain initiator or a chain terminator. However, if the reactive additive has more than one free —SH group, it will be incorporated into the polymer backbone.

In one embodiment, the additive is prepared by totally or partially esterifying a polyol with a mercaptoaliphatic carboxylic acid, preferably a marcaptoalkyl carboxylic acid (also referred to herein as a thioalkylcarboxylic acid), and then reacting some or all of the mercapto functionalities with an unsaturated compound.

This invention includes, but is not limited to, at least the following embodiments. Other embodiments will be readily apparent given the general teaching herein. All such embodiments are considered to fall within the scope of the invention.

A nonlimiting example of a additive that can be used in the polymeric composition is that prepared by A) reacting:
(i) a polyol selected from the group consisting of pentaerythritol, sorbitol, mannitol, glycol, alkylene glycol, polyalkylene glycol, trimethylolalkane, dipentaerythritol, cyclohexane-1,2,4-trimethanol, tripentaerythritol, hexahydroxycyclohexane, pentahydroxycyclopentane, trihydroxycycloheptane, glycerine, benzene-1,2,4,5-tetramethanolpentaerythritol, glycol, or a mixture thereof, with
(ii) a thioaliohatic carboxvlic acid; and then B) reacting the product of step A with a monomer selected from the group consisting of 3-methyl-3-butene-1-ol, methacrylic acid, acrylic acid, alkyl acrylate, alkyl methacrylate, 2-hydroxypropyl (meth)acrylate, 2-hydroxyethyl(meth)acrylate, unsaturated cycloaliphatic epoxy compounds, allyl alcohol, $CH_2=CHC_6H_4C(CH_3)_2NCO$, octyldecylacrylate, 2,4, 6-tribromophenyl (meth)acrylate, and 2-(2,4,6-tribromophenoxy)ethyl ester of 2-propenoic acid.

For example, the thioaliphatic carboxylic acid can be selected from the group consisting of thioglycolic acid, thiolactic acid, α-mercaptopropionic acid, β-mercaptopropionic acid, mercaptoacetic acid, mercaptovaleric acid, mercaptobutyric acid, and mercaptohexanoic acid. A useful alkyl methacrylate is n-butyl acrylate.

This compound can be alternatively illustrated as a compound of the following formula:

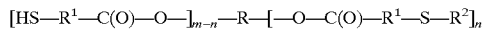

wherein:
R is the residue of a polyol;
m+n is the number of hydroxyl groups in the polyol;
$R^1$ is an aliphatic moiety; and
$R^2$ is the residue of an unsaturated moiety selected from the group consisting of 3-methyl-3-butene-1-ol, methacrylic acid, acrylic acid, alkyl acrylate, alkyl methacrylate, 2-hydroxypropyl(meth)acrylate, 2-hydroxyethyl(meth)acrylate, unsaturated cycloaliphatic epoxy compounds, allyl alcohol, $CH_2=CHC_6H_4C(CH_3)_2NCO$, octyldecylacrylate, 2,4, 6-tribromophenyl (meth)acrylate, and 2-(2,4,6-tribromophenoxy)ethyl ester of 2-propenoic acid.

A second nonlimiting example of a additive that can be used in the polymeric composition is a noncrosslinked compound, prepared by:

(A) reacting a polyol with a thioaliphatic carboxylic acid to produce product A;
(B) reacting product A with a compound that contains one unsaturated bond capable of reacting with a thiol, in such a fashion that approximately 1 or 2 free thiol groups remain in the product; and then
(C) reacting the product of step B with a diacrylate or dimethacrylate in such a fashion that all of the remaining thiol groups are reacted.

Nonlimiting examples of diacrylates and dimethacrylates are epoxy di(meth)acrylate, polyester di(meth)acrylate, urethane di(meth)acrylate, alkyleneoxide bis-phenolic di(meth) acrylate, and epoxy bis-phenol di(meth)acrylate. Nonlimiting examples of compounds that contain one unsaturated bond capable of reacting with a thiol are those selected from the group consisting of 3-methyl-3-butene-1-ol, methacrylic acid, acrylic acid, alkyl acrylate, alkyl methacrylate, 2-hydroxypropyl (meth)acrylate, 2-hydroxyethyl(meth) acrylate, unsaturated cycloaliphatic epoxy compounds, allyl alcohol, $CH_2=CHC_6H_4C(CH_3)_2NCO$, octyldecylacrylate, 2,4,6-tribromophenyl (meth)acrylate, 2-(2,4,6-tribromophenoxy)ethyl ester of 2-propenoic acid, styrene, alkylstyrene, halostyrene, dihalostyrene, and divinylstyrene or a mixture thereof.

This compound can be alternatively illustrated as a compound of the following formula:

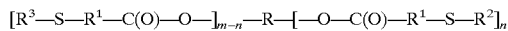

wherein:
R is the residue of a polyol;
$R^1$ is an aliphatic moiety;
$R^2$ is the residue of a compound that contained one unsaturated bond that has reacted with a thiol;
$R^3$ is the residue of a diacrylate or dimethacrylate after reaction with a free thiol group;
m+n=the number of hydroxyl groups in the polyol;
m−n must be at least one; and
n must be greater than zero.

A preferred additive is the adduct of pentaerythritol tetra(3-mercaptopropionate) (hereinafter "PTM") and styrene, which has three or four styrenes per PTM.

Another embodiment of the present invention is a polymer composition containing one or more polymers in combination with one or more additives described herein. While these additives can be added to any polymer composition, they are preferably added to optical grade polymer compositions. Non-limiting examples of such optical grade polymer compositions include: a diethyleneglycol bis(allyl carbonate) resin, polymers made from polyurethanes that are optionally end capped with acrylates, polyalkylene glycol diacrylate or dimethacrylate, epoxy acrylates or methacrylates, and bisphenol-A polycarbonates.

A further embodiment of the present invention is an optical lens which contains the additive of the present invention either in the form of a non-reactive compound or as a reactive compound incorporated into the polymer.

As a general expression of the invention, the casting composition for otptical grade polymeric materials comprises:

(a) about 60–75% by weight of a di(meth)acrylate, and preferably a urethane di(meth)acrylate;

(b) about 5–20% by weight of a monothiol; and (c) about 15–30% by weight of an aromatic compound with conjugated unsaturation.

The monothiol that is included in this polymeric casting composition can be prepared, for example, by reacting a polyol with a thioaliphatic carboxylic acid; and then reacting the product with any unsaturated monomer. Preferred monomers are those selected from the group consisting of styrene, alkylstyrene, halostyrene, dihalostyrene, divinylstyrene or a mixture thereof. The reaction is perferably carried out in a manner such that all of the hydroxyl groups of the polyol are esterified with the thiocarboxylic acid, and also in such a manner that the final product contains a free —SH group.

The urethane di(meth)acrylate in this composition can, for example, have the formula:

wherein:

A is an aliphatic (typically alkyl) or aromatic ester portion of the hydroxylated acrylate or methacrylate used to end-cap the oligomer;

n is 0 to 6;

P is an aliphatic or aromatic polyether, including a polyol;

R is the residue of the isocyanate to which the isocyanate moieties are attached, and $R^1$ is H or $CH_3$.

Another non-limiting formulation for the manufacture of eyeglass lenses is a material comprising one or more of the additives disclosed herein with a polymerizable composition comprising:

(a) about 30 to 80 percent of one or more multifunctional urethane or epoxy(meth)acrylate oligomers, including diacrylate or dimethacrylate, having a molecular weight between 200 and 10,000 (preferably, the oligomer has a molecular weight between 200 and 5000 and most preferably between 200 and 2000); and (b) about 10 to 70 percent of one or more reactive diluents, such as an unsaturated aromatic monomer, a multifunctional acrylate or methacrylate monomer, or a vinyl ether.

The chemical structures of some selected additives that can be included in the polymeric compositions for the preparation of optical grade materials are shown below:

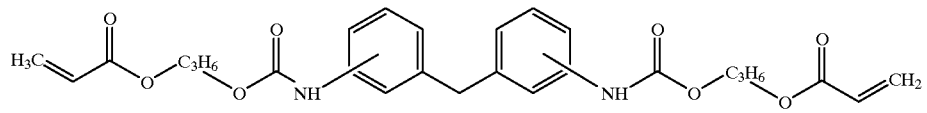

Alternatively, the urethane di(meth)acrylate can have the formula:

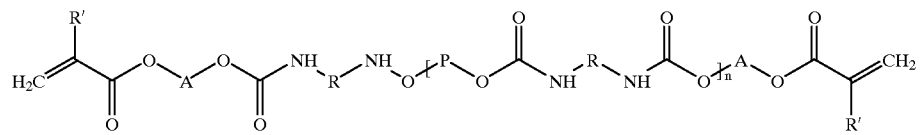

7
8
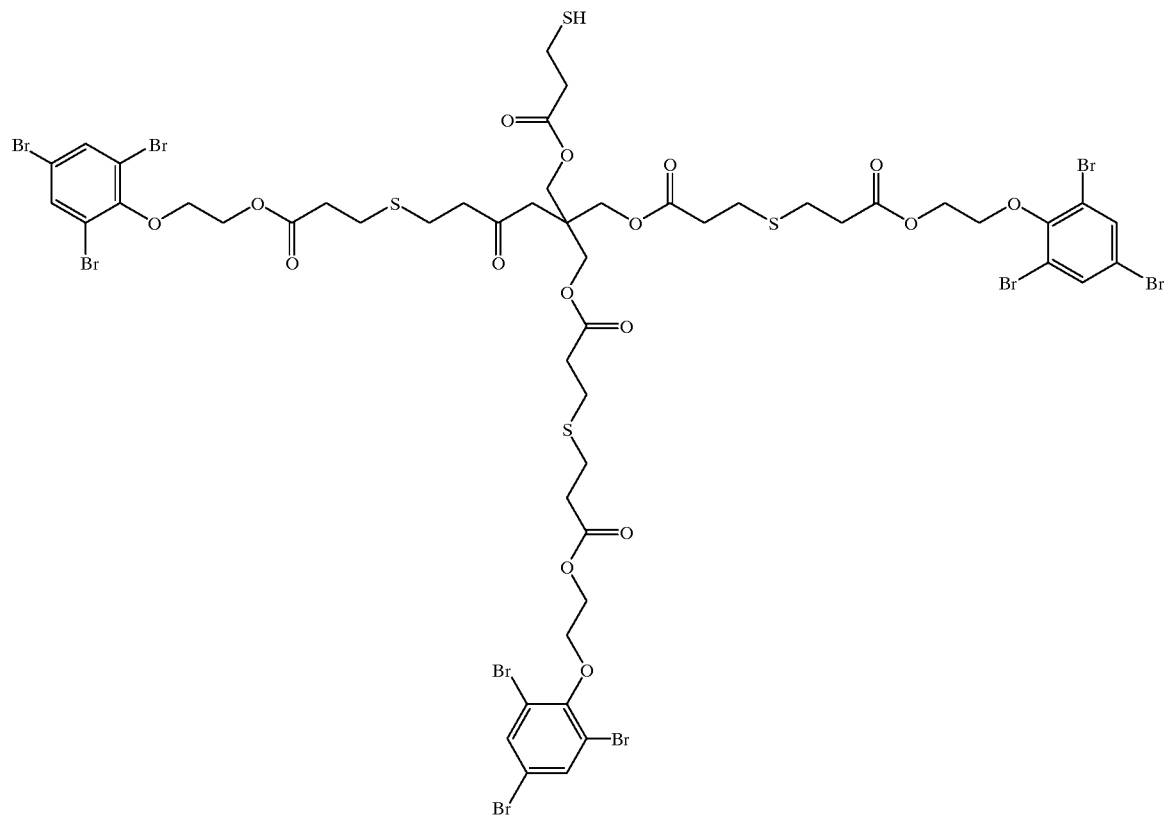

-continued
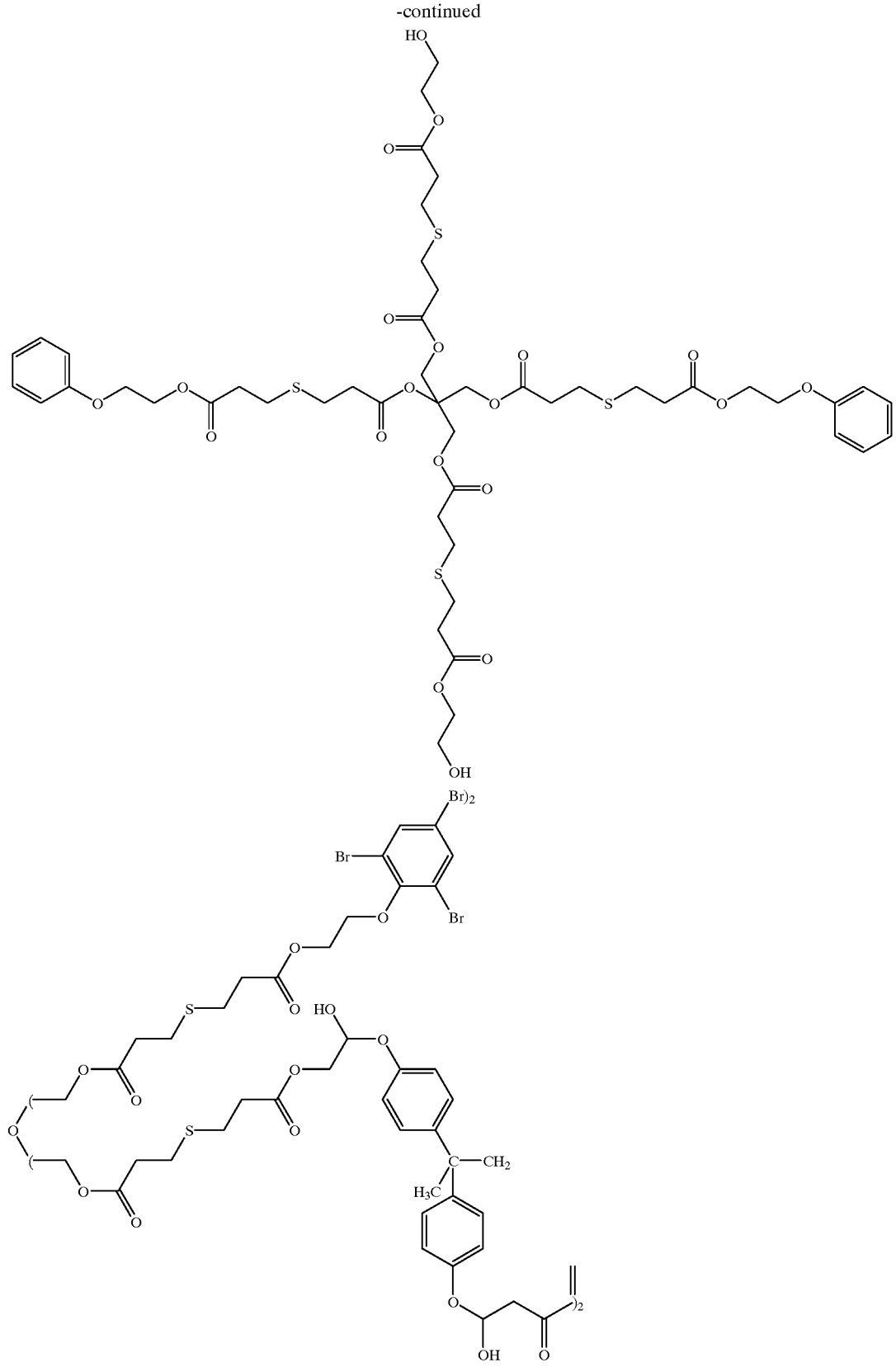

Hereinafter will be found some definitions of the terms used in the following description.

The term alkyl, as used herein, refers to a saturated straight, branched, or cyclic hydrocarbon, or a combination thereof, typically of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term lower alkyl, as used herein, refers to as saturated straight, branched, or cyclic hydrocarbon, or a combination thereof, typically of $C_1$ to $C_6$, and specifically includes methyl, ethyl, propyl, isopropyl, butyl, isobutyl, t-butyl, pentyl, cyclopentyl, isopentyl, neopentyl, hexyl, isohexyl, and cyclohexyl.

The term substituted alkyl, as used herein, is an alkyl group, wherein the substituent is halo, cyano, C(O) (alkyl), —$CO_2H$, —$OSO_2H$, —$SO_3H$, —$PO_3H$, —O(O)C-alkyl, —C(C)O-alkyl, —C(O)S-alkyl, —SC(O)-alkyl, epoxy, including cycloaliphatic epoxy, amide, amino, alkylamino and dialkylamino.

The term aryl or aromatic, as used herein, refers to any compound that exhibits aromaticity, and includes phenyl, naphthyl, biphenyl, or substituted phenyl, napthyl or biphenyl, wherein the substituent is halo, alkyl, substituted alkyl, heteroalkyl, alkoxy, alkylthio, haloalkyl, hydroxyalkyl, alkoxyalkyl, methylenedioxy, —SH, epoxy, cyano, C(O)(alkyl), —$CO_2H$, —$OSO_2H$, —$SO_3H$, —$PO_3H$, —$CO_2$alkyl, amide, amino, alkylamino and dialkylamino, and wherein the aryl group can have up to 5 substituents.

As used herein, the term "alkyl acrylate" refers to $H_2C$=$CHCO_2R$, wherein R is a straight, branched, or cyclic alkyl group, preferably $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl, and other longer chain homologues, including octadecyl acrylate.

As used herein, the terms diacrylate and dimethacrylate include mixtures of acrylate and methacrylate.

As used herein, the term (meth)acrylate refers to either acrylate, methacrylate, or a mixture of acrylate and methacrylate.

As used herein, the term "alkyl methacrylate" refers to $H_2C$=$C(CH_3)CO_2R$, wherein R is a straight, branched, or cyclic alkyl group, preferably $C_1$ to $C_{20}$, and specifically includes methyl, ethyl, propyi, isopropyl, butyl, isobutyl, t-butyl, pentyl, cyclopencyl, isopentyl, neopentyl, hexyl, isohexyl, cyclohexyl, 3-methylpentyl, 2,2-dimethylbutyl, and 2,3-dimethylbutyl, and other long chain homologues.

The term cycloaliphatic epoxy moiety refers to a cycloalkyl group, typically of $C_5$ to $C_8$, that is substituted with an epoxy group. Preferably, the cycloalkyl group is a $C_6$ cycloalkyl group. The cycloalkyl group may be further substituted with additional groups, as described above for substituted alkyl groups. Non-limiting examples of suitable cycloaliphatic epoxy groups include cyclohexane-1,2-epoxide, 3,4-epoxycyclohexylmethyl-3,4-epoxy-cyclohexane carboxylate, vinyl cyclohexene dioxide, 2-(3, 4-epoxycyclohexyl-5,5-spiro-3,4-epoxy)cyclohexane-metadioxane, bis(3,4-epoxycyclohexyl)adipate, and vinyl cyclohexene monoxide. An unsaturated cycloaliphatic epoxy moiety is a cycloaliphatic moiety as described above that also contains a double bond either in the cycle or attached thereto directly or through an aliphatic spacer.

The term halo, as used herein, includes fluoro, chloro, bromo, and iodo.

The term aralkyl refers to an aryl group with an alkyl, substituted alkyl or heteroalkyl substituent.

The term alkaryl refers to an alkyl, substituted alkyl or heteroalkyl group that has an aryl substituent, including benzyl, substituted benzyl, phenethyl or substituted phenethyl, wherein the substituents are as defined above for aryl groups.

The term heteroalkyl, as used herein, refers to an alkyl group that includes one or more heteroatoms such as oxygen, sulfur, or nitrogen (with valence completed by hydrogen or oxygen) in the carbon chain or terminating the carbon chain. Examples of these compounds include a series of lower alkyls interrupted by a heteroatom such as oxygen, sulfur or nitrogen, including —O—[(alkyl)O]$_x$—(alkyl) wherein the alkyl group can vary within the moiety, including —O—[($CH_2)_xO]_y$—$CH_3$), wherein x is 1–8 (which can vary within the moiety) and y is an integer of 1 to 40.

The term polyol refers to a compound with more than one hydroxyl group, and includes but is not limited to aliphatic glycols, trials, tetrols, pentols, and hexols. The term polyol specifically includes ethylene glycol, propylene glycol, alkylene glycol, polypropylene glycol, polyethylene glycol, polyalkylene glycol, trimethylolpropane, pentaerythritol, sorbitol, mannitol, trimethylolethane, trimethylolbutane, trimethylolpropane, trimethylolalkane, dipentaerythritol, cyclohexane-1,2,4-trimethanol, tripentaerythritol, hexahydroxycyclohexane, pentahydroxycyclopentane, trihydroxycycloheptane, glycerine, other carbohydrates, trimethylolisopropylmethane, trimethylolheptadecane, and benzene-1,2,4,5-tetramethanol.

The term allohatic refers to a hydrocarbon, typically of $C_1$, to $C_{20}$, and typically, $C_1$, to $C_{10}$ that can contain one or a combination of alkyl, alkenyl, or alkynyl moieties, and which can be straight, branched, or cyclic, or a combination thereof.

The term thioaliphatic carboxylic acid refers to an aliphatic carboxylic acid that contains an —SH group. The term includes, but is not limited to HS—($C_nH_{2n}$)—$CO_2H$, wherein n is 1, 2, 3, 4, 5, 6, 7, 8, 9, or 10, and wherein the —SH moiety can alternatively be located on an internal carbon, as opposed to the terminal, carbon atom. Additionally, one or more hydroxyl groups can be attached to carbon atoms in the chain. Specific examples include thioglycolic acid, thiolactic acid, α-mercaptopropionic acid, β-mercaptopropionic acid, mercaptoacetic acid, mercaptovaleric acid, mercaptobutyric acid, and mercaptohexanoic acid.

The thiol containing compounds used to form the additives are organic compounds which include one or more thiol (—SH) groups. The thiol containing compound is preferably the reaction product of a polyol and a thioaliphatic carboxylic acid, wherein all or some of the hydroxyl groups of the polyol are esterified.

In one embodiment, the thiol is prepared by reacting:
(i) a polyol, such as an aliphatic glycol, triol, tetrol, pentol, or hexol (specifically including ethylene glycol, propylene glycol, alkylene glycol, trimethylolpropane, pentaerythritol, sorbitol, mannitol, trimethylolethane, trimethylolbutane, trimethylolpropane, trimethylolalkane, dipentaerythritol, cyclohexane-1,2, 4-trimethanol, tripentaerythritol, hexahydroxycyclohexane, pentahydroxycyclopentane, trihydroxycycloheptane, glycerine, other carbohydrates, trimethylolisopropylmethane, trimethylolheptadecane, and benzene-1,2,4,5-tetramethanol) with
(ii) a thiocarboxylic acid of the formula HS—($C_nH_{2n}$)—$CO_2H$, wherein n is 1, 2, 3, 4, 5, 6, 7, 8, 9, or 10, and wnerein the —SH moiety can alternatively be located on an internal carbon, as opposed to the terminal carbon atom. Additionally, one or more hydroxyl groups can be attached to carbon atoms in the chain. Examples of suitable compounds include, but are not limited to thioglycolic acid, thiolactic acid, α-mercaptopropionic acid, β-mercaptopropionic acid, mercaptoacetic acid, mercaptovaleric acid, mercaptobutyric acid, and mercaptohexanoic acid.

Non-limiting examples of thiols which are suitable for use in the present invention include, but are not limited to:

glycol dimercaptoacetate, glycol dimercaptopropionate, pentaerythritol tetra-(3-mercaptopropionate), pentaerythritol tri-(3-mercaptopropionate), pentaerythritol tetrathioglycolate, polyethylene glycol dimercaptoacezate, trimethylolpropane tri-(3-mercaptopropionate) and trimethylolpropane trithioglycolate.

Two preferred thiols are pentaerythritol tetra(3-mercaptopropionate) (hereinafter "PTM") and glycol dimercaptoacetate (hereinafter "GDMA").

In another embodiment, the thiols are of the formula

R—(SH)$_p$ wherein:

R is selected from alkyl, substituted alkyl, heteroalkyl, aryl, alkaryl, or aralkyl radicals, or radicals of formula $(R^8)_{y-C-(R^6-Z-R^7-)_x}$, and —R$^7$—Z—(R$^9$—Z)$_q$—R$^7$—, wherein x is 1, 2, 3 or 4, y is 0, 1, 2 or 3 and q is 0, 1, 2 or 3;

R$^6$, R$^7$, R$^8$ and R$^9$ may vary within the molecule and are each independently selected from alkyl, substituted alkyl, heteroalkyl, aryl, alkaryl or aralkyl radicals;

each Z is independently selected from a direct link, —C(O)—, —O(O)C—, and —C(O)O—; and p is 1, 2, 3 or 4.

Non-limiting examples of R$^6$, R$^7$, R$^8$ and R$^9$ include: hydrogen; substituted or unsubstituted methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimechylbutyl, heptyl, octyl, nonyl, and decyl radicals, wherein the substituent is fluorine, chlorine, bromine, iodine, —CN, C(O)(alkyl), —CO$_2$H, —OSO$_2$H, —SO$_3$H, —PO$_3$H, —O(O)C-alkyl, —C(O)O-alkyl, —C(O)S-alkyl, —SC(O)-alkyl, epoxy, —NH$_2$, alkylamino and dialkylamino; and phenyl.

The thiol can also be a compound of the following formulae:

(R$^8$)$_y$—C—(R$^6$—Z—R$^7$—SH)$_x$ and

HS—R$^7$—Z—(R$^9$—Z)$_q$—R$^7$—SH wherein:

R$^6$, R$^7$, and R$^8$, are each independently lower alkylene groups, preferably linear alkylene groups comprising from 1 to 6 carbon atoms;

each Z is independently selected from —OC(O)—, —C(O)O— and —C(O)—;

R$^9$ is selected from lower alkyl and poly(lower alkylene oxide) groups;

x is 1, 2, 3 or 4;

y is 0, 1, 2 or 3;

and q is 0, 1, 2 or 3.

Preferably, R$^9$ is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —(CH$_2$CH$_2$O)$_n$— and —(CH$_2$CH$_2$CH$_2$O)$_n$—, where n is 1 to 20.

In one embodiment, the unsaturated compound is selected from the group consisting of 3-methyl-3-butene-1-ol, methacrylic acid, butyl acrylate, 2-phenoxyethylacrylate, 2-hydroxyethyl(meth)acrylate and styrene. In another embodiment, the unsaturated compound is selected from divinylbenzene and bisphenol-A-epoxy diacrylate.

In another embodiment, the unsaturated compound is of formula

HCR$^2$=C(R$^3$)—X—R$^4$—Y wherein:

R$^2$ is selected from H, alkyl, substituted alkyl, heteroalkyl, alkaryl, aralkyl, or aryl radicals;

R$^3$ is selected from H and CH$_3$.

R$^4$ is selected from a direct link, alkyl, substituted alkyl, heteroalkyl, aryl, alkaryl, and aralkyl radicals;

X is a direct link, —O—, —S—, —C(O)O—, —O(O)C—, —SC(O)—, or —C(O)S—; and

Y is H, —NCO, —OH, —CO$_2$H, —X—CR$^3$=CHR$^2$,

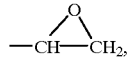

—O—(O)CH, —SH or —NR$^1_2$.

Non-limiting examples of R$^2$ include: hydrogen; substituted or unsubstituted methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl radicals, wherein the substituent is halo, —CN, C(O)(alkyl), —CO$_2$H, —OSO$_2$H, —SO$_3$H, —PO$_3$H, —O(O)C-alkyl, —C(O)O-alkyl, —C(O)S-alkyl, —SC(O)-alkyl, epoxy, —NH$_2$, alkylamino and dialkylamino; and phenyl.

Non-limiting examples of R$^4$ include: a direct link, substituted or unsubstituted methyl, ethyl, propyl, isopropyl, butyl, isobutyl, t-butyl, pentyl, cyclopencyl, isopentyl, neopentyl, hexyl, isonexyl, cyclohexyl, 3-methylpentyl, 2,2-dimethylbutyl, 2,3-dimethylbutyl, heptyl, octyl, nonyl, and decyl radicals, wherein the substituent is halo, —CN, C(O)(alkyl), —CO$_2$H, —OSO$_2$H, —SO$_3$H, —PO$_3$H, —O(O)C-alkyl, —C(C)O-alkyl, —C(O)S-alkyl, —SC(O)-alkyl, epoxy, —NH$_2$, alkylamino and dialkylamino; phenyl or phenyl substituted with methyl, ethyl, or one or more halogens; and cycloaliphatic epoxy.

The unsaturated compound can also be a compound of formula:

HCR$^2$=C(R$^3$)—X—R$^4$—Y    (IV)

wherein

R$^2$ is selected from H, lower alkyl, phenyl and substituted phenyl;

R$^3$ is selected from H and CH$_3$.

R$^4$ is selected from a direct link, lower alkyl, phenyl, substituted phenyl, and cycloaliphatic epoxy;

X is a direct link or —C(O)O—; and

Y is H, —OH, —CH=CH$_2$, —O(C)C—C(R$^3$)=CH$_2$ and —O—(O)CH.

Preferably, R$^2$, is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, phenyl and phenyl substituted with methyl, ethyl or one or more halogens.

Preferably, R$^4$, is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, and —CH$_2$CH$_2$CH$_2$CH$_2$CH$_2$CH$_2$—, phenyl, phenyl substituted with one or more methyl, ethyl or halogen, and 1,2-epoxycyclohexane.

Non-limiting examples of suitable unsaturated compounds include: cinnamaldehyde, acrylic acid, α-methyl styrene, alkyl acrylates and methacrylates, diacrylates, p-methyl styrene, dibromostyrene, cinnamyl formate, 2-hydroxy methacrylate, 4-vinyl cyclohexene-1,2-epoxide, allyl alcohol, and 1-(1-isocyanato-1-methylethyl)-3-(1-methylethenyl)benzene.

Non-limiting examples of alkyl acrylates and methacrylates and diacrylates include: methyl acrylate, ethyl acrylate, propyl acrylate, isopropyl acrylate, butyl acrylate, isobutyl acrylate, t-butyl acrylate, pentyl acrylate, cyclopentyl acrylate, isopentyl acrylate, neopentyl acrylate, hexyl acrylate, isohexyl acrylate, cyclohexyl acrylate, 3-methylpentyl acrylate, 2,2-dimethylbutyl acrylate, 2,3-dimethylbutyl acrylate, methyl methacrylate, ethyl methacrylate, propyl methacrylate, isopropyl methacrylace, butyl methacrylate, isobutyl methacrylate, t-butyl methacrylate, pentyl methacrylate, cyclopentyl methacrylate, isopentyl methacrylate, neopentyl methacrylate, hexyl methacrylate, isohexyl methacrylate, cyclohexyl methacrylate, 3-methylpentyl methacrylate, 2,2-dimethylbutyl methacrylate, 2-amino ethyl methacrylate, t-amyl methacrylate, 2-dimethyl aminoethyl methacrylate, 2-ethylhexyl acrylate, 2-ethylhexyl methacrylate, 1,6-hexanediol diacrylate, hydroxypropyl acrylate, isoamyl methacrylate, methyl-2-(bromomethyl)acrylate, 3-sulfopropyl acrylate, 3-sulfopropyl methacrylate, 2,3-dimethylbutyl methacrylate, hexanediol diacrylate, diacrylate of ethoxylated bisohenol A, tripropylene glyccl diacrylate, diacrylate of epoxidized bisphenol A, and dihydroxyethyl acrylate adduct of hexamethylene diisocyanate.

Additives can be prepared via the reaction of a carbon—carbon double bond in the unsaturated compound with one of the thiol groups in the thiol containing compound. This reaction can be accomplished by any known method, including by the following general procedure:

(1) The unsaturated compound is mixed with an initiator.
(2) the thiol is mixed with the unsaturated compound-initiator mixture; and
(3) the mixture is exposed to an appropriate energy source (for example, heat or photoradiation) to initiate polymerization.

By appropriate selection of the unsaturated compound and the thiol (including the appropriate selection of a polyol and a mercaptoaliphatic carboxylic acid), an additive can be provided that exhibits:

(i) an Abbe number of between 25 and 60, preferably between 30 and 52, and more preferably between 30 and 48; and
(ii) a refractive index of between about 1.4 and 1.7, and more preferably between 1.5 and 1.7.

By appropriate selection of the components, the color of the additive can also be minimized. The color of the material can be evaluated according to any known procedure, for example, that described in detail below.

A sample is placed in a cuvet and the color and lightness are measured instrumentally (for example, 10 mm pathlength quartz cuvet with a Chroma Meter CT-310 available from Minolta). A quartz cell identical to the one the sample will be placed in should be used as the control. Fill the quartz cell with deionized water and calibrate the instrument. Ensure that there is no foreign particulate matter in the sample. If particulate matter is present, filter the material using an appropriate method. Allow any air incorporated in the sample during transfer into the cell to escape. Heat or a vacuum oven may be used to aid in the removal of air bubbles. Condition the sample for one hour at room temperature. Place the sample cell in the instrument and measure the color. Record the values of a and b. An acceptable color is an "a" value greater than −0.5 and a "b" value that is less than 2.0, and preferably, less than 1.5.

The ratio of unsaturated monomer to thiol containing compound can range from about 0.1:1 (moles double bond:moles SH) to about 2.0:1.0 (moles double bond:moles SH). Preferably, the ratio is in the range from about 0.25:1 (moles double bond:moles SH) to about 1.0:1.0 (moles double bond:moles SH). One preferred ratio is between 0.5:1 and 0.9:1, and more preferably, 0.75:1.0 (moles double bond:moles SH).

Any initiator which can initiate the reaction between the thiol and the carbon—carbon double bond in the unsaturated compound is suitable for use to form the additives. $H_2S$ and mercaptans can add to olefins via electrophilic, nucleophilic and free radical mechanisms.

Nucleophilic addition of mercaptans to olefins is quite effective when catalyzed by small amounts of a very nucleophilic compound. The nucleophilic catalyst activates the double bond toward attack by nucleophiles. The use of acrylic or styrenyl substrates with electron withdrawing functional groups leads to a Michael-type addition to form thioether linkages. Acrylate monomers are most reactive towards base-catalyzed addition. One example of a suitable nucleophilic catalyst is tris[dimethylamino(methyl)]phenol (Ancamine® K-54, sold by Air Products Corporation). Other nonlimiting examples of catalysts include 4-dimethylaminopyridine (DMAP), 1,4-diazabicyclo[2.2.2]octane (triethylenediamine), 1,5-diazabicyclo[4.3.0]non-5-ene(DBN), and 1,8-diazabicyclo[5.4.0]undec-7-ene(DBU). Amine-containing monomers such as Ebecryl® Product P104, P115, and EB 7100 sold by UCB Chemicals, Inc., may also be used for the twofold purpose of catalyzing mercaptan-olefin addition and covalently incorporating itself into the cured polymer structure.

In another embodiment, the reaction is initiated using a free radical initiator. The initiator can be activated, for example by exposure to photoradiation (photoinitiation), such as UV or visible light, or by exposure to heat (thermal initiation). Certain compounds (such as the reaction of an allyl with the thiol) may not require the use of an initiator, but may spontaneously react upon mixing of the two components. Other sources of radiation that induce free radical generation can be used, such as, ionizing radiation (electron beam, x-ray, gamma rays) or sufficient thermal energy. However, these methods may be impractical from a cost standpoint.

Non-limiting examples of suitable initiators include: di-(2-ethylhexyl)peroxydicarbonate, di-n-propyl peroxydicarbonate, di-sec-butyl peroxydicarbonate, di-(2-phenoxyethyl)peroxydicarbonate, 3-hydroxy-1,1-dimethylbutyl peroxyneodecanoate, α-cumyl peroxyneodecanoate, 3-hydroxy-1,1-dimethylbutyl peroxyneoheptanoate, α-cumyl peroxyneoheptanoate, t-amyl peroxyneodecanoate, t-butyl peroxyneodecanoate, t-amyl peroxyneoheptanoate, t-amyl peroxypivalate, t-butyl peroxypivalate, 3-hydroxy-1,1-dimethylbutyl peroxy-2-ethylhexanoate, 2,5-dimethyl-2,5-di-(2-ethylhexanoylperoxy)hexane, t-amyl peroxy-2-ethylhexanoate, t-butyl peroxy-2-ethylhexanoate, t-butyl peroxyisobutyrate, t-butyl peroxy-(cis-3-carboxy) propenoate, 2,5-dimethyl-2,5-di(benzoylperoxy)hexane, t-amyl peroxyacetate, t-amyl peroxybenzoate, t-butyl peroxyacetate, t-butyl peroxybenzoate, di-t-butyl diperoxyphthaiate, diisononanoyl peroxide, didodecanoyl peroxide, didecanoyl peroxide, succinic acid peroxide, dibenzoyl peroxide, OO-t-amyl O-(1,2,2,6,6-pentamethyl-4-piperidinyl)monoperoxycarbonate, OO-t-amyl-O-(2-ethylhexyl)monoperoxycarbonate, OO-t-butyl-O-isopropyl monoperoxycarbonate, OO-t-butyl-O-(2-ethylhexyl) monoperoxycarbonate, 1,1-di-(t-amylperoxy)cyclohexane, 1,1-di-(t-butylperoxy)-3,3,5-trimethylcyclohexane, 1,1-di-(t-butylperoxy) cyclohexane, 2,2-di-(t-butylperoxy) butane, 2,2-di-(t-amylperoxy)propane, n-butyl-4,4-di-(t-butylperoxy)valerate, ethyl-3,3-di-(t-amyl-peroxy)butyrate, ethyl-3,3-di-(t-butylperoxy)butyrate, di-α-cumyl peroxide, α,α'-di-(t-butylperoxy) diisopropylbenzene, 2,5-dimethyl-2,5-di-(t-butylperoxy)hexane, di-t-amyl peroxide, t-butyl-α-cumyl peroxide, di-t-butyl peroxide, 2,5-dimethyl-2,5-di-(t- butylperoxy)-3-hexyne, 2,5-dihydroperoxy-2,5-dimethylhexane, cumene hydroperoxide, t-butyl hydroperoxide, t-amyl hydroperoxide, benzil dimethyl ketal, 1-hydroxy-cyclohexyl-phenyl ketone, dimethoxy-hydroxy acetophenone, 2-methyl-1-[(4-(methylthio)phenyl]-2-morpholino-propanone, 2-benzyl(2-methyl-2-morpholino-propanonyl)-9-butyl-carbazole, 2,4,6-trimethylbenzoyl-diphenyl-phosphine oxide, benzophenone, blend of 2-isopropyl- and 4-isopropylthioxanthone, 2-hydroxy-2-methyl-1-phenyl-1-propanone, and blend of 2-chloro and 4-chlorothioxanthone.

The reaction of the thiol with the unsaturated compound should be allowed to proceed until the limiting reagent (either thiol or unsaturated compound) is consumed. Typically, the reaction is completed in a period of from approximately 0.5 hours to 24 hours, more typically from 0.5 to 6 hours and most typically from 3 hours to 5 hours. The reaction should be allowed to proceed at any temperature that achieves the desired results, and typically at temperatures from about 40 to about 120° C.

Additives such as UV absorbers, tinting agents, and anti-oxidants can also be added to the polymerization mixture to obtain the desired properties of the final product. These additives can, for example, be added to the reaction to control the color of the end product. Non-limiting examples of suitable antioxidants include triphenyl phosphite, and trisnonyl phenyl phosphite.

The additives described above are suitable for use in polymeric compositions for optical purposes, for example, in polymers used to make eyeglass lenses.

The compounds can be used as reactive additives or non-reactive additives. Non-reactive additives are added to the polymeric materials in the same way as conventional additives and do not react with the polymerization mixture. When selecting a non-reactive additive for use in an optical composition, such as an eyeglass lens, the non-reactive additive should have a refractive index which is the same or substantially the same as that of the final polymeric composition. If the refractive indices of the final polymer and the additive are substantially different, the final product will have a hazy appearance, which is an undesirable for optical grade polymers.

If reactive additives are incorporated into the polymer, the additive need not have a refractive index which matches the final polymer. By appropriate selection of the reactive additive and the monomer or oligomer, a polymer can be prepared that has a desired refractive index and relative dispersion and color. For example, if the refractive index of the monomer or oligomer and the additive are known, the ultimate refractive index of the polymer can be predicted with reasonable accuracy from the proportions of these components.

Thiol terminated reactive additives can react with monomer or oligomer mixtures which are cured via a free radical reaction. Hydroxyl terminated additives can react with urethane reaction mixtures or epoxy systems cured using cationic initiators.

The formation of lenses or other polymeric optical materials containing the additive uses the following steps:

1) mixing the additive with a monomer, oligomer or polymer along with appropriate initiators, and other additives which are used to form the optical article; and 2) curing, polymerizing, extruding, injection molding, thermoforming, or using any other appropriate method of processing the material to form the optical article.

The additive can be added to the polymer in an amount such that it constitutes from 0.5 to 90 percent by weight of the final composition. Preferably, the additive is present in an amount from about 0.5 to 60 percent by weight. More preferably, the additive is present in an amount from about 0.5 to 40 percent by weight of the final composition. For eyeglass lens compositions the additive is preferably present from 8 to 15 percent by weight.

Non-limiting examples of the monomers, oligomers, and polymers that the additives can be added to are: acrylate, vinyl, methacrylate, vinyl ether, vinyl ester, allyl, or any other carbon-carbon double bond containing monomer or oligomer, polyurethanes, epoxies, polyimides, polyolefins, unsaturated polyesters, polyamides, polyesters, and phenolics.

One, non-limiting use of these polymers is as an additive for a polymer formulation for making ophthalmic lenses. The formulation contains compounds which contain reactive double bond species which, upon polymerization, form an optical grade polymer. Non-limiting examples of such polymers are epoxy and urethane acrylate or methacrylate monomer or oligomers, vinyl compounds, allyl compounds, unsaturated polyesters and vinyl ether compounds.

A wide variety of specific polymeric compositions are known to be suitable for use as optical lenses, for example, eyeglass lenses. The additives may be used with any of these polymer systems. Examples of specific polymer systems are set forth in U.S. Pat. Nos. 3,891,523; 4,073,967; 4,107,235; 4,146,696; RE 30,212; 4,228,256; 4,268,134; 4,376,800; 4,382,135; 4,435,450; 4,544,572; 4,737,558; 4,758,448; 4,769,431; 4,781,978; 4,800,123; 4,826,936; 4,830,481; 4,837,289; 4,857,606; 4,873,029; 4,912,185; 4,923,906; 4,936,666; 4,977,229; 4,997,299; 5,023,305; 5,049,321; 5,061,336; 5,063,112; 5,070,166; 5,071,531; 5,076,684; 5,139,338; 5,147,585; 5,149,181 and 5,278,243.

The formulation can also contain additives, such as UV absorbers, hindered amine light stabilizers, antioxidants, mold release agents, and dyes, in order to improve the properties of the final lens article.

The formulation described above is mixed with the additive and polymerized. Preferably, the material is polymerized in a glass mold which has the desired curvature for the final lens.

One non-limiting polymerization regimen is as follows. The mold containing the polymeric formulation is exposed to UV light for from about 1 to 30 minutes, preferably about 1 to 15 minutes and most preferably about 5 to 15 minutes. The molds are then exposed to a heat source, such as an infrared lamp, while UV exposure is continued. This process is conducted from 0 to 90 minutes, preferably from 0 to 60 minutes, more preferably from 10 to 20 minutes. At the end of this exposure, the molds are transferred into an oven which is heated to a temperature in the range from about 80 to 150° C., preferably from 90 to 135° C., most preferably from about 100 to 120° C. The molds are kept in the oven for between 0 and 4 hours, preferably between 0 and 3 hours and most preferably from 5 minutes to 2 hours. Following the heat treatment, the molds are removed from the oven, allowed to cool, and the finished lens is de-molded.

The following examples are non-limiting working examples which further illustrate the disclosed invention.

Pentaerythritol tetra(3-mercaptopropionate) (referred to below as "PTM") was obtained from Evans Chemetics. Styrene was obtained from Arco Chemicals, Inc. p-Methylstyrene was obtained from Deltech Corporation. Dibromostyrene was obtained from Great Lakes Chemical. Celloxide 2000 was obtained from Daicel Industries, Inc., Ltd. HEMA was obtained from Rohm and Haas. Iragure 184 and Darocure 1173 were obtained from Ciba-Geigy. Lupersol 575 was obtained from Elf Atochem. Divinyl benzene was obtained from Dow Chemical. 3-Methyl-3-butene-1-ol and 2,4,6-trimethylbenzoyl-diphenyl-phosphine oxide (TPO) were obtained from BASF. Methacrylic acid was obtained from DuPont. Diazobiscyclooctane (DABCO) and hydroauinone (HQ) were obtained from Aldrich. All materials were used as received.

The refractive index of the additive was measured using a Abbe Refractometer, manufactured by Fisher Scientific.

The viscosity of the additives was measured using a Model DV-II Viscometer, manufactured by Brookfield.

EXAMPLE 1

Preparation of PTM/Styrene Product by Photoinitiation

Styrene (372 g, 3.573 eq.) was weighed into a 2000 ml, three neck, round bottom flask along with TPO (2.43 g). The flask was sealed with rubber stoppers and placed in a 60° C. oven for approximately 20 minutes. The contents were swirled occasionally until the TPO dissolved into the styrene. The flask was removed from the oven and allowed to cool to less than 40° C. at which point PTM (600 g, 4.764 eq.) was weighed into the flask.

A stainless steel stirring blade was inserted into the flask's center neck. A Type K thermocouple was inserted through one of the two side necks of the flask and into the material in order to monitor the reaction temperature. The other side neck was equipped with an air condenser. Two 365 nm, 400 watt metal halide light sources (Electro Lite Corporation, Model ELC 4000 Curing Unit) were placed facing the flask. The contents of the flask were vigorously agitated using the air motor. The two lights were then turned on and the reaction exotherm was noted within seconds.

The two lights were turned off and on to regulate the speed and temperature of the reaction. in this way the reaction temperature was kept below 60° C. After the reaction exotherm began to die down, the material was exposed to both lights for an additional 30 minutes. The entire reaction lasted approximately 4 hours.

At the end of the reaction the refractive index was 1.5645, measured at 25° C., and the Abbe number was 37. The SH remaining was evaluated by titration with iodine and found to be 1.38 meq/g, compared to a theoretical value of 1.22 meq/g. The viscosity was measured to be 1972 cps at 25° C. using a number four spindle at 100 rpm. The material was then stored in dark high density polyethylene bottles.

EXAMPLE 2

Preparation of PTM/Styrene Product by Photoinitiation

The procedure described in Example 1 was conducted using styrene (491.3 g, 4.717 eq); TPO (1.36 g); and PTM (600 g, 4.764 eq.).

During this reaction, an air hose was directed at the flask to aid in the cooling of the reaction. Again the reaction temperature was kept below 60° C. After the reaction exotherm began to die down, the material was exposed to both lights for an additional 30 minutes. This reaction lasted approximately 3 hours.

At the end of the reaction the refractive index was 1.5698, measured at 25° C., and the Abbe number was 37. The SH remaining was not determined but gas chromatography determined the free styrene to be less than 0.5%. The viscosity was measured to be 3268 cps at 25° C. using a number four spindle at 100 rpm. The material was then stored in dark high density polyethylene bottles.

EXAMPLE 3

Preparation of PTM/Styrene Product by Photoinitiation

Styrene (351 g, 3.37 eq.) was weighed into a 2000 ml, three neck round bottomed flask along with 1.8 grams of Irgacure 184 (1.8 g). The Irgacure 184 was soluble in styrene at room temperature so that preheating was not necessary. PTM (847.2 g, 6.73 eq.) was weighed into the flask. The flask was set up for reaction and agitation as described in Example 1. An air hose was directed at the flask to aid in the cooling of the reaction and the reaction temperature was kept below 60° C. After the reaction exotherm began to die down, the material was exposed to both lights for an additional 30 minutes. This reaction lasted approximately 3 hours.

At the end of the reaction the refractive index was 1.5568, measured at 25° C., and the Abbe number was 37. The SH remaining was determined to be 2.77 meq/g at the end of the reaction, compared tc the theoretical SH value of 2.8 meq/g. The viscosity was measured to be 1320 cps at 25° C. using a number four spindle at 100 rpm. The material was then stored in dark high density polyethylene bottles.

EXAMPLE 4

Preparation of PTM/2-hydroxyethyl methacrylate (HEMA) Product by Photoinitiation The procedure described in Example 3 was followed, using HEMA (508.5 g, 3.91 eq.); Irgacure 184 (2.5 g); and PTM (482 g, 3.91 eq.).

The flask was set up for reaction and agitation as described in Example 1. In this reaction, the reaction temperature was allowed to increase to a maximum of 75° C. After the reaction exotherm began to die down, the material was exposed to both lights for an additional 30 minutes. This reaction lasted approximately 3 hours.

The remaining SH was determined to be 0.18 meq/g at the end of the reaction. The material was then stored in dark high density polyethylene bottles.

EXAMPLE 5

Preparation of GDMA/Styrene Product by Photoinitiation

Styrene (481.4 g, 4.62 eq.) was weighed into a 2000 ml, three neck, round bottom flask along with TPO (1.52 g). The flask was sealed with rubber stoppers and placed in a 60° C. oven for approximately 20 minutes. The contents were swirled occasionally until the TPO dissolved into the styrene. The flask was removed from the oven and allowed to cool to less than 40° C. at which point GDMA (518.6 g, 4.467 eq.) was weiched into the flask.

The flask was set up for reaction and agitation as described in Example 1. An air hose was directed at the flask to aid in the cooling of the reaction. The reaction temperature was kept below 60° C. After the reaction exotherm began to die down, the material was exposed to both lights for an additional 30 minutes. This reaction lasted approximately 3 hours.

At the end of the reaction the refractive index was 1.567, measured at 25° C., and the Abbe number was 36.5. The residual SH was not determined. The viscosity was measured to be 216 cps at 25° C. using a number four spindle at 100 rpm. The material was then stored in dark high density polyethylene bottles.

EXAMPLE 6

Preparation of GDMA/Dibromo Styrene Product by Thermal Initiation

GDMA (204.6 g, 1.89 eq.) was weighed into a 2000 ml, three neck, round bottom flask. Dibromostyrene (495.4 g, 1.89 eq.) and 3.2 grams of Lupersol 575 (Elf-Atochem) were weighed into a 500 ml addition funnel equipped with a teflon stopcock.

The flask containing the PTM was heated to approximately 90° C. under agitation. The addition funnel containing the dibromo styrene/Lupersol 575 mixture was placed on the second neck of the flask and a slow drip was started. A reaction exotherm was immediately obtained and the addition rare was controlled so that the exotherm temperature did not exceed 105° C.

At the end of the reaction the refractive index was 1.6175, measured at 25° C., and the Abbe number was 34. The SH remaining was titrated with Iodine to be 0.064 meq/g. The material was then stored in dark high density polyethylene bottles.

EXAMPLE 7

Preparation of PTM/Styrene Product by Thermal Initiation

The procedure described in Example 6 was carried out using PTM (600 g, 4.746 eq.), styrene (372 g, 3.753 eq.), and Lupersol 575 (1.61 g).

The refractive index was 1.5637, measured at 25° C., and the Abbe number was 37. The SH remaining was titrated with Iodine to be 1.29 meq/g compared to a theoretical value of 1.22 meq/g. The viscosity was measured to be 1668 cps at 25° C. using a number four spindle at 100 rpm. The material was then stored in dark high density polyethylene bottles.

EXAMPLE 8

Preparation of GDMA/Divinyl benzene Product by Photoinitiation

GDMA (741.8 g, 7.86 eq.) was weighed into a 2000 ml, three neck round bottom flask along with Darocure 1173 (2.5 g). Divinyl benzene (258.2 g, 3.43 eq.) was weighed into a 500 ml addition funnel equipped with a Teflon stop cock.

The flask was set up for reaction and agitation as described in Example 1. The two lights were then turned on and the divinyl benzene was added over two hours. The addition rate was increased or decreased in order to control the exotherm and keep the reaction temperature below 80° C. After the reaction exotherm began to die down, the material was exposed to both lights for an additional 30 minutes. This reaction lasted approximately 2.5 hours.

At the end of the reaction the refractive index was 1.5578, measured at 25° C., and the Abbe number was 37.5. The SH remaining was determined to be 3.265 meq/g, compared to the theoretical value of 3.43 meq/g. The material was then stored in dark high density polyethylene bottles.

EXAMPLE 9

Preparation of GMDA/3-methyl-3-butene-1-ol Product by Thermal Initiation

GDMA (281.1 g, 2.6 eq.) was weighed into a 2000 ml, three neck, round bottom flask. 3-Methyl-3-butene-1-ol (223.9 g, 2.6 eq.) was weighed into a 500 ml addition funnel equipped with a teflon stopcock.

The flask was set up for reaction and agitation as described in Example 6. No heat was initially added to the flask containing the GDMA. The addition funnel containing the 3-methyl-3-butene-1-ol was placed on the second neck of the flask and a slow drip was started. The reaction exotherm was mild and the addition was completed in 40 minutes. The flask was then heated to 60° C. and held for one hour. Iodine titration indicated a significant amount of free thiol remaining (3.72 meq/g). Lupersol 575 (2.5 g) was added slowly. A significant exotherm occurred, after which the free thiol was measured to be 0.047 meq/gram. The material was then stored in dark high density polyethylene bottles.

EXAMPLE 10

Preparation of GDMA/Methacrylic Acid (MAA) Product by Photoinitiation

GDMA (556.8 g, 5.15 eq.) was weighed into a 2000 ml, three neck, round bottom flask. MAA (442.9 g, 5.15 eq.) and Irgacure 184 (1.5 g) were weighed into a 500 ml addition funnel equipped with a Teflon stop cock.

The flask was set up for reaction and agitation as described in Example 1. The two lights were then turned on and the MAA mixture was added over two hours. The addition race was increased or decreased to control the exotherm and keep the temperature below 80° C. After the reaction exotherm began to die down, the material was exposed to both lights for an additional 30 minutes. This reaction lasted approximately 2.5 hours.

The SH remaining at the end of the reaction was determined to be 1.44 meq/g. The material was then stored in dark high density polyethylene bottles.

EXAMPLE 11

Preparation of Urethane Oligomer from Polythiol from Example 3

Diphenylmethane diisocyanate (350 g, 2.8 eq., sold as Mondur ML) and 0.53 grams of DABCO were weighed into a 3000 ml, three neck flask. HEMA (201.6 g, 1.4 eq.) and 0.42 grams of hydroquinone were weighed into a 500 ml addition funnel.

The flask containing the Mondur ML was moderately agitated. HEMA was added over one hour, taking care to limit the temperature to between 66 and 73° C. The temperature was then maintained for 30 minutes after the HEMA was fully added. The product from Example 3 (506.1 g, 1.4 eq.) was weighed into an addition funnel. This was then used to replace the addition funnel which had contained the HEMA. The material was added to the flask over 75 minutes. The temperature was increased to between 88 and 93° C. and held for two hours. The residual free-NCO was determined to be 0.16 and the residual free SH was determined to be 0.206 meq/g.

Styrene (117.75 g) was added to the flask and mixed until homogeneous. The refractive index of the mixture was 1.5787, measured at 25° C. and the Abbe number was 34. The viscosity was determined to be 4730 cps at 65.7° C. using a number 28 spindle at 50 rpm in a Brookfield Thermal Cell. The material was stored in a lined quart can.

EXAMPLE 12

Preparation of Four Hydroxy Functional Extended PTM/Styrene Product by Thermal Initiation PTM (1027 g, 8.0 eq.) was weighed into a 3000 ml, three neck round bottom flask. 3-Methyl-3-butene-1-ol (344.4 g, 4.0 eq.), styrene (208.3 g, 2 eq.) and Lupersol 575 (2.4 g) were weighed into a 1000 ml addition funnel equipped with teflon stopcock. The flask was set up for reaction and agitation as described in Example 6. The flask containing the PTM was heated to approximately 90° C. under agitation. The addition funnel containing the monomer mixture and Lupersol 575 was placed on the second neck of the flask and a slow drip was started. A reaction exotherm was immediately obtained and the addition rate was controlled so that the exotherm temperature did not exceed 105° C.

Ninety minutes after the monomers were added, the residual SH was measured to be 1.38 meq/gram, compared to a theoretical value of 1.26 meq/gram. Divinyl benzene (152.4 g, 2 eq.) was then weighed into the addition funnel and dripped into the reaction, while maintaining the reaction temperature under 100° C.

After approximately 3 hours the residual SH was measured to be 0.01 meq/gram. The refractive index was 1.551, measured at 25° C. The viscosity was measured to be 1380 cps at 65.6° C. using a number 28 spindle at 50 rpm. The material was then stored in dark high density polyethylene bottles.

EXAMPLE 13

Preparation of PTM dicapped with Compound A by Nucleophilic Addition

PTM (35.2 g, 0.28 eq) was reacted with 60.0 g of Compound A (illustrated below, 0.14 eq) in the presence of 0.13 g Ancamine K-54 (0.2 wt. %) at 100° C. for twelve hours to give an additive containing PTM with two thioether linkages and two unreacted mercapto moieties per molecule. n20/D=1.584. The viscosity at 60° C. was 1900 cp, and —SH 1.5 units were 1.5 meq/g (indicating 100% conversion).

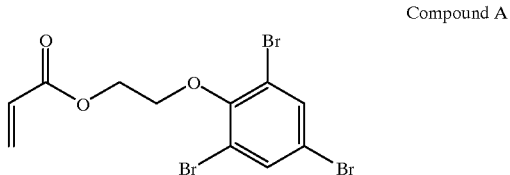

Compound A

EXAMPLE 14

Preparation of GDMA 1.5-Capped with Compound A by Nucleophilic Addition

GDMA (50 g, 0.46 meq) was reacted with 149 g Compound A (0.35 meq) in the presence of 0.4 g Ancamine K-54 (0.2 Wt. %) at 70° C. for forty five minutes to give GDMA with an average thioether functionality ratio of 1.5 and a mercapto functionality of 0.5 per end unit. n20/D=1.593. Ninety-five percent conversion was obtained; —SH=0.67 meq/g).

EXAMPLE 15

Preparation of Compound B Capped with the product of Example 14

The product of Example 14 (72.8 meq) was reacted with 40 g of Compound B (illustrated below, 155 meq) at 70° C. for five hours. No additional catalyst was added. Ancamine K-54 level was approximately 0.15 weight percent. The final product consisted of unreacted Compound B, the product of Example 14 capped with Compound B and possessing a polymerizable acrylic group, and GDMA dicapped with Compound B. n20/D=1.584.

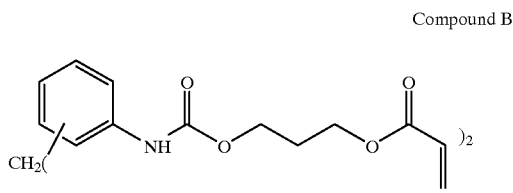

Compound B

EXAMPLE 16

Preparation of PTM Tricapped with Compound A by Nucleophilic Addition

PTM (400 g, 3.1 eq) was reacted with 1000 g Compound A (2.3 eq) in the presence of 2.8 g (0.2 wt %) Ancamine K-54 at 95° C. for eight hours. It required an 85% conversion to achieve a structure with an average of 2.5 thioether groups and 1.5 mercapto groups per four initial thiol end units. Viscosity=3400 cP at 60° C., n20/D=1.592.

EXAMPLE 17

PTM Dicapped with 2-(Phenoxyethyl Acrylate (PEA) and Hydroxyethyl acrylate (HEA)

PTM (682 g, 5.3 eq), HEA (307 g, 2.6 eq), and PEA (508 g, 2.6 eq) were reacted for ten hours in the presence of 3.0 g Ancamine K-54 (0.2 wt. %) at 95° C. The final product possessed an average theoretical structure of two PEA-thioether groups and two HEA groups. Viscosity=8600 cP at 25° C., n20/D=1.536. (—SH$_{final}$=0.29; 92% conversion).

EXAMPLE 18

PTM Dicapped with Both BR-31 and EB 600 (Bisphenol A Epoxy Diacrylate)

PTM (400 g, 3.1 eq) was reacted with Compound A (667 g, 1.55 eq) at 95° C. in the presence of 0.2 wt. % Ancamine K-54 to give the disubstituted PTM. This product was then reacted with 814 g EB 600 (3.1 eq) at 100° C. to give PTM disubstituted with both moieties and containing a maximum of two unreacted, polymerizable acrylate functionalities. The product was diluted 20 wt. % with styrene to give a pourable material with a viscosity of 13,500 cP at 25° C., and 860 cp at 60° C. n20/D=1.571. The reaction time was seven hours.

EXAMPLE 19

Preparation of a Polymer Containing a PTM/Styrene Additive

An oligomeric mixture was formed by mixing the following: a urethane acrylate based on diphenylmethane diisocyanate (MDI) and hydroxypropylacrylate (75.12% w/w), p-methyl styrene (24.12% w/w), TPO (0.08% w/w), triphenyl stilbene (0.11% w/w) and 2-(2'-hydroxy-5'-tert-octylphenyl) benzotriazole (0.59% w/w) sold under the tradename Tinuvin 329 by Ciba Geigy.

The oligomer mixture (90.6 g) was mixed with the additive formed in Example 1 (9.4 g). The material was then poured into a quartz mold having the curvature desired in the final lens. The mold was placed under UV light for 10 minutes. Infrared lamps were then used to heat the lens mold from above while the UV exposure was continued from underneath. This exposure was continued for 15 minutes. After curing, the lens mold was placed in an oven at 105° C. for one hour. The mold was removed from the oven and allowed to cool. The lens exhibited the following properties:

Refractive Index=1.572
Abbe Number=34
Glass Transition Temperature=105° C.
Impact Resistance=Pass
Color—Excellent The Impact test was performed by dropping a ⅝ inch steel ball (approximately 16 grams) onto the center of the lens from a height of 50 inches. The test was performed at room temperature. If the lens breaks into pieces it fails the test. If the lens remains in one piece, even if it cracks, it passes the test.

EXAMPLE 20

Preparation of a Polymer Containing a PTM/Styrene Additive

An oligomeric mixture was formed by mixing the following: a urethane acrylate formed by reacting MDI and hydroxypropyl methacrylate (57.59% w/w), a urethane acrylate based on MDI, hydroxypropyl acrylate and a polyethylene glycol diol with 10% w/w p-methyl styrene (19.33% w/w), p-methyl styrene (22.42% w/w), TPO (0.07% w/w), and 2-(2'-hydroxy-5'-tert-octylphenyl)benzotriazole (0.59% w/w) sold under the tradename Tinuvin 329 by Ciba Geigy.

This oligomeric mixture (76.05 g) was mixed with the additive formed in Example 1 (10.8 g). The material was then poured into a quartz mold having the curvature desired in the final lens. The mold was placed under UV light for 13 minutes. After curing, the lens mold was placed in an oven at 130° C. for six minutes. The mold was removed from the oven and allowed to cool and demolded. The lens exhibited the following properties:

Refractive Index=1.57
Abbe Number=34
Glass Transition Temperature=120° C.
Impact Resistance=Pass
Color—Excellent

EXAMPLE 21

Preparation of a Polymer Containing a PTM/Styrene Additive

An oligomeric mixture was formed by mixing the following: a urethane acrylate formed by reacting MDI and hydroxypropylmethacrylate (72.04% w/w), a silicone resin (2.22% w/w) sold under the tradename Z-6018 by Dow Corning, p-methyl styrene (25.33% w/w), TPO (0.06% w/w), and 2-(2'-hydroxy-5'-tert-octylphenyl)benzotriazole (0.35% w/w) sold under the tradename Tinuvin 329 by Ciba Geigy.

The procedure described in Example 14 was carried out using the oligomeric mixture set forth above (22.58 g) and the additive formed in Example 1 (10.8 g). The lens exhibited the following properties:

Refractive Index=1.57
Abbe Number=34
Glass Transition Temperature=105° C.
Impact Resistance=Pass
Color—Excellent

EXAMPLE 22

Preparation of Additive based on PTM and n-butyl acrylate

The procedure of Example 6 was followed using the following reagents: 1.7 equivalents (217.9 grams) of n-butyl acrylate with 2.24 equivalents (281.8 grams) PTM and Lupersol 757 as the catalyst. The product exhibited a refractive Index at 20° C. of 1.5015, an Abbe number of 46, viscosity @ 25° C. 430 cP. residual SH=1.27 (theoretical=1.15).

EXAMPLE 23

Eye Glass Formulation

A pourable eyeglass formulation is prepared using the following steps.

1) An oligomer similar to that described in Example 13 (see below) is prepared using 1 equivalent of Mondur ML (A blend of 55% 2,4' and 45% 4,4' isomers of diphenylmethane diisocyanate (MDI) supplies by Bayer), and 1 equivalent of hydroxypropylacrylate. To this is added 0.09% by weight of catalyst (DBTDL); MEHQ (0.21% of total weight), (0.8% in HPA add. 0.13% as post); TPS –0.15% of total weight; BHT –0.92% of total weight; UV Absorber: Tinuvin 329 0.66% of total weight; Photoinitiator: Lucerin TPO 0.24% of total weight.

2) The material from step 1 (9.8% by weight), is mixed with 2% of the product of Example 17 B); 66.15% Compound B (see above for chemical structure); and 22.05% p-methylstyrene.

A cured lens made from this formulation has a refractive index at 20° C. of 1.572; Abbe number of 32; glass transition temperature of 95° C.; and excellent color. A lens with a 1.5 mm center thickness passed the Dress Lens impact test.

I claim:

1. A compound prepared by:
   A) reacting:
      (i) a poly selected from the group consisting of pentaerythritol, sorbitol, mannitol, glycol, alkylene glycol, polyalkylene glycol, trimethylolalkane, dipentaerythritol, cyclohexane-1,2,4-trimethanol, tripentaerythritol, hexahydroxycyclohexane, pentahydroxycyclopentane, trihydroxycycloheptane, glycerine, benzene-1,2,4,5-tetramethanolpentaerythritol, glycol, or a mixture thereof, with
      (ii) a thioaliphatic carboxylic acid; and
   B) reacting the product of step A with a monomer selected from the group consisting of 3-methyl-3-butene-1-ol, methacrylic acid, acrylic acid, alkyl acrylate, alkyl methacrylate, 2-hydroxypropyl(meth)acrylate, 2-hydroxyethyl(meth)acrylate, unsaturated cycloaliphatic epoxy compounds, allyl alcohol, $CH_2=CH_2C_6H_4C(CH_3)_2NCO$, octyldecylacrylate, 2,4,6-tribromophenyl (meth)acrylate, and 2-(2,4,6-tribromophenoxy)ethyl ester of 2-propenoic acid.

2. a noncrosslinked compound, prepared by:
   A) reacting a polyol with a thioaliphatic carboxylic acid to produce product A;
   B) reacting A with a compound that contains one unsaturated bond capable of reacting with a thiol, in such a fashion that approximately 1 or 2 free thiol groups remain in the product and then
   C) reacting the product of step B with a diacrylate or dimethacrylate in such a fashion that all of the remaining thiol groups are reacted.

3. The compound of claim 2, wherein the diacrylate or dimethacrylate is selected from the group consisting of epoxy di(meth)acrylate, polyester di(meth)acrylate, urethane di(meth)acrylate, alkyleneoxide bis-phenolic di(meth)acrylate, and epoxy bis-phenol di(meth)acrylate.

4. The compound of claim 2, wherein the compound that contains one unsatruated bond capable of reacting with a thiol is selected from the group consisting of 3-methyl-3-butene-1-ol, methacrylic acid, acryllic acid, alkyl acrylate, alkyl methacrylate, 2-hydroxypropyl(meth)acrylate, 2-hydroxyethyl(meth)acrylate, unsaturated cycloaliphatic epoxy compounds, allyl alcohol, $CH_2=CH_2C_6H_4C(CH_3)_2NCO$, octyldecylacrylate, 2,4,6-tribromophenyl(meth)acrylate, 2-(2,4,6-tribromophenoxy)ethyl ester of 2-propenoic acid, styrene, alkylstyrene, halostyrene, dihalostyrene, and divinylstyrene or a mixture thereof.

5. The compound of claim 1 or claim 2, that has an Abbe number of between 25 and 60.

6. The compound of claim 1 or claim 2, that has a refractive index between 1.4 and 1.7.

7. A polymerizable composition comprising a compound according to claim 1.

8. A polymerizable composition comprising a non-crosslinked compound according to claim 2.

9. A compound selected from compounds of the formula:

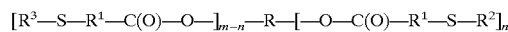

$[R^3-S-R^1-C(O)-O-]_{m-n}-R-[-O-C(O)-R^1-S-R^2]_n$ wherein:

R is the residue of a polyol;

$R^1$ is an aliphatic moiety;

$R^2$ is the residue of a compound that contained one unsaturated bond capable of reacting with a thiol;

$R^3$ is the residue of a diacrylate or dimethacrylate after reaction with a free thiol group;

m+n=the number of hydroxyl groups in the polyol;

m−n must be at least one; and n must be greater than zero, and compounds of the formula:

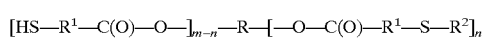

$[HS-R^1-C(O)-O-]_{m-n}-R-[-O-C(O)-R^1-S-R^2]_n$ wherein:

m+n is the number of hydroxyls in the polyol;

R is the residue of a polyol;

$R^1$ is an aliphatic moiety;

$R^2$ is the residue of an unsaturated moiety selected from the group consisting of 3-methyl-3-butene-1-ol, methacrylic acid, acrylic acid, alkyl acrylate, alkyl methacrylate, 2-hydroxypropyl(meth)acrylate, 2-hydroxyethyl(meth)acrylate, unsaturated cycloalilphatic epoxy compounds, allyl alcohol, $CH_2=CH_2C_6H_4C(CH_3)_2NCO$, octyldecylacrylate, 2,4,6-tribromophenyl (meth)acrylate, and 2-(2,4,6-tribromophenoxy)ethyl ester of 2-propenoic acid.

* * * * *